United States Patent
Stanish et al.

(10) Patent No.: US 6,533,744 B1
(45) Date of Patent: Mar. 18, 2003

(54) PORTABLE APPARATUS FOR APPLYING TRACTION FORCES TO A HUMAN OR ANIMAL BODY

(76) Inventors: Walt Stanish, 1617 Mt. Silliman Way, Antioch, CA (US) 94509; Scott Steinheiser, 2330 Pleasant Hill Rd. #16, Pleasant Hill, CA (US) 94523

( * ) Notice: Subject to any disclaimer, the term of this patent is extended or adjusted under 35 U.S.C. 154(b) by 0 days.

(21) Appl. No.: 09/784,404

(22) Filed: Feb. 15, 2001

(51) Int. Cl.[7] .................................................. A61F 5/00
(52) U.S. Cl. ........................................... 602/33; 602/35
(58) Field of Search ............................... 602/32, 33, 35, 602/38–40; 128/845, 846; 482/140, 142, 145; 248/164; 5/648, 649, 650, 651; 606/241

(56) References Cited

U.S. PATENT DOCUMENTS

| | | | | |
|---|---|---|---|---|
| 988,923 A | * | 4/1911 | Bauerfeind | ................. 248/118 |
| 3,390,675 A | * | 7/1968 | Giannestras | ................. 602/33 |
| 4,621,625 A | * | 11/1986 | Powlan | ......................... 602/33 |
| 5,010,898 A | * | 4/1991 | de Kanawati et al. | ...... 128/845 |
| 5,290,220 A | * | 3/1994 | Guhl | .......................... 128/882 |
| 5,775,334 A | * | 7/1998 | Lamb et al. | ................. 128/845 |
| 5,961,512 A | * | 10/1999 | Purnell | ............................ 606/1 |
| 6,238,361 B1 | * | 5/2001 | Poirier | ......................... 602/33 |

* cited by examiner

*Primary Examiner*—Danton D. DeMille
*Assistant Examiner*—Quang D. Thanh
(74) *Attorney, Agent, or Firm*—Thomas R. Lampe

(57) ABSTRACT

Portable traction apparatus for applying traction forces to a human or animal body includes a support member and an elongated, double-ended traction arm pivotally connected to the support member. The traction arm is mounted for movement about orthogonally disposed pivots. A lock is employed to selectively lock the traction arm against movement relative to the support member at selected orientations. An attachment clamp is connected to the support member for releasably attaching the support member to a structure.

6 Claims, 4 Drawing Sheets

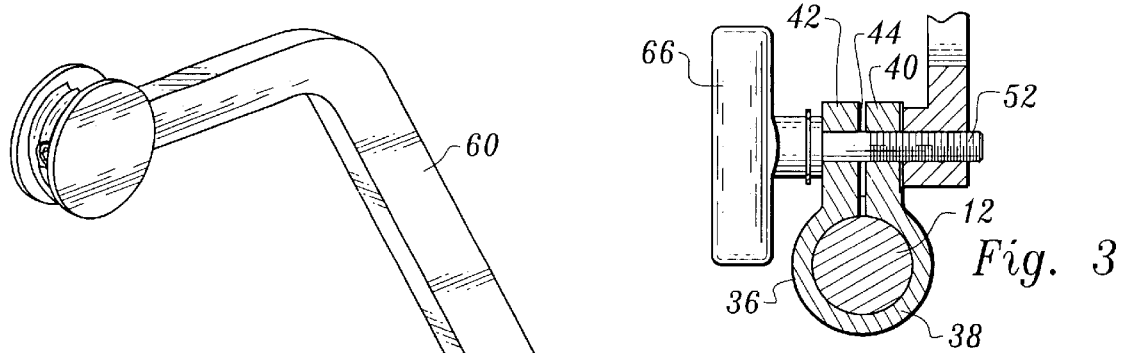
Fig. 3
Fig. 1
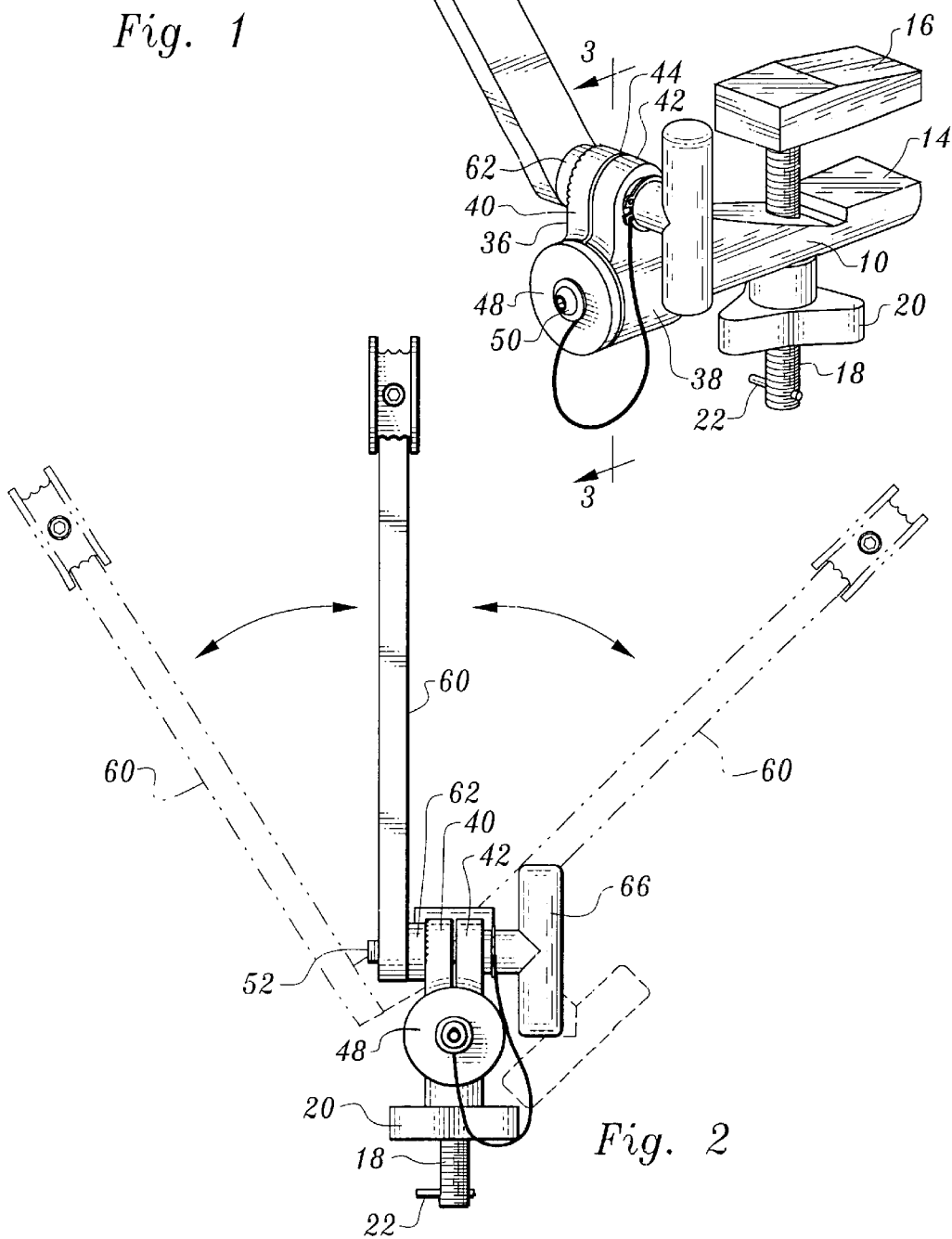
Fig. 2

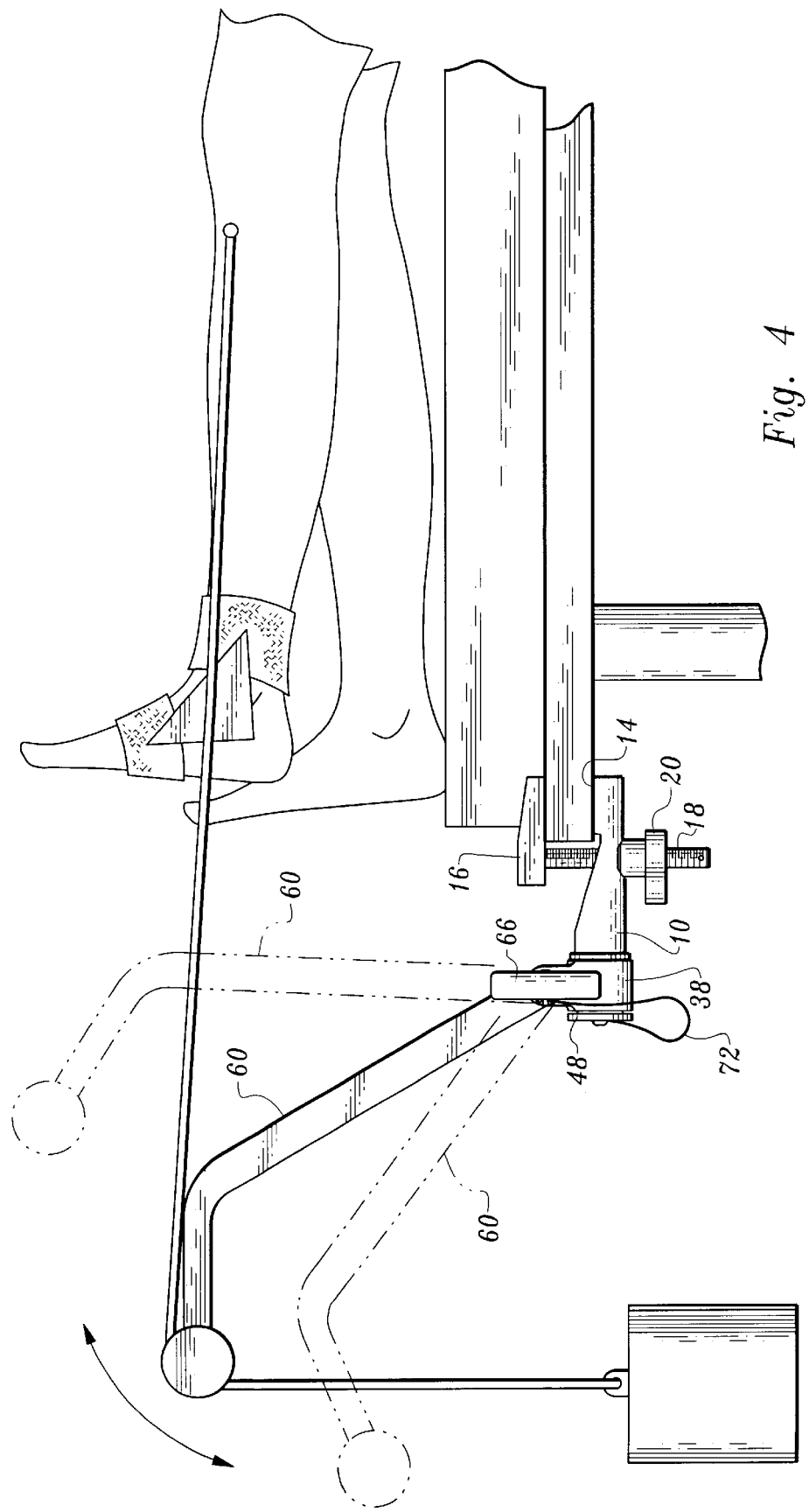

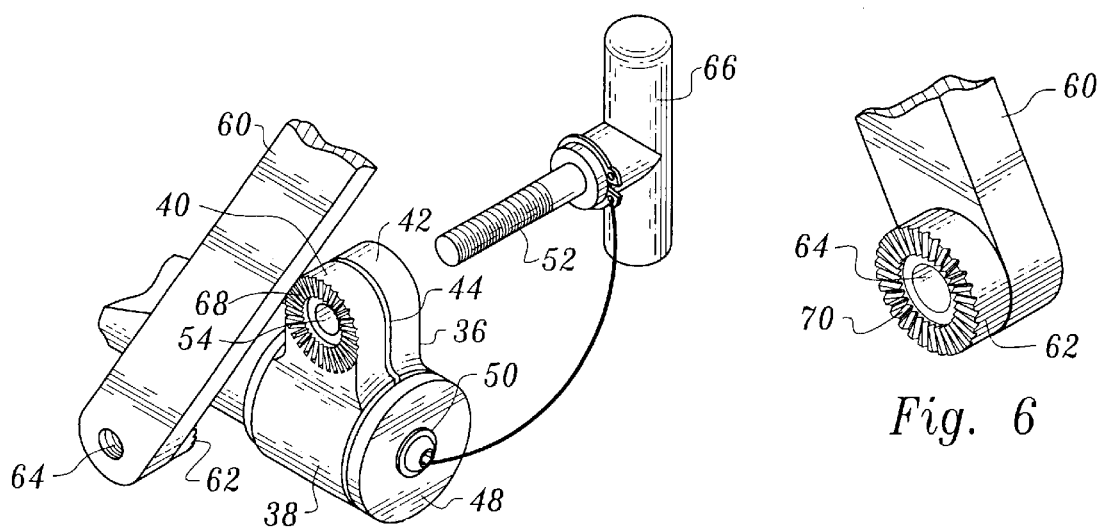
Fig. 5
Fig. 6
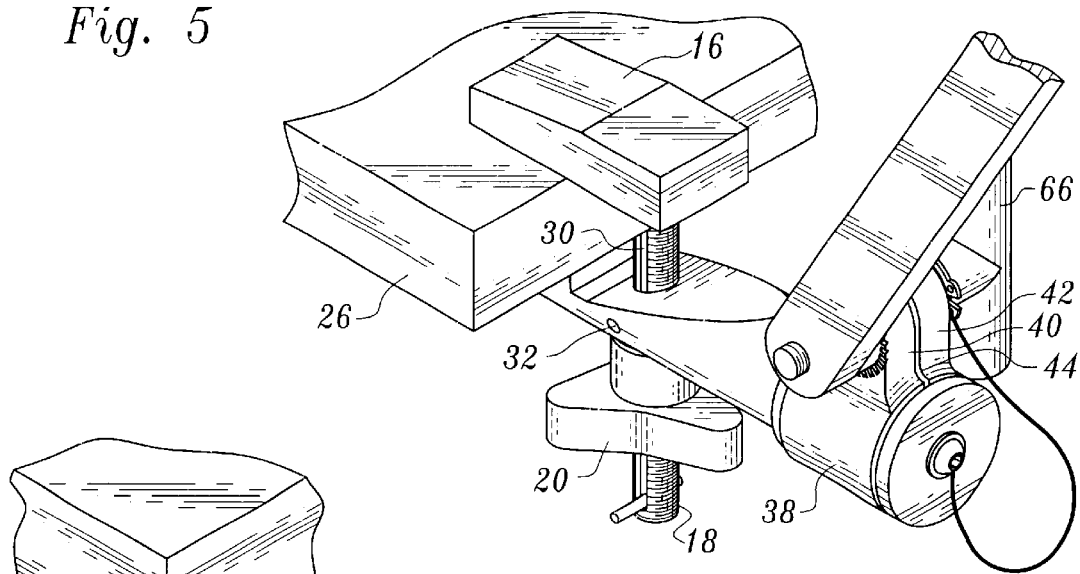
Fig. 7
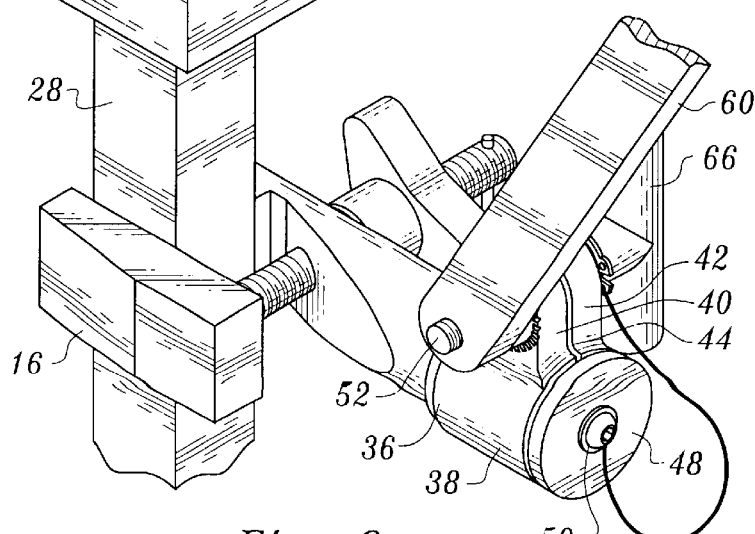
Fig. 8

PORTABLE APPARATUS FOR APPLYING TRACTION FORCES TO A HUMAN OR ANIMAL BODY

TECHNICAL FIELD

This invention relates to apparatus which is employed to apply traction forces to a human or animal body.

BACKGROUND OF THE INVENTION

A variety of systems have been devised over the years for applying traction forces to an individual. Traction systems are typically in the form of elaborate and expensive tables which support the patient and complex and relatively expensive traction force applicator devices associated with the tables to apply the desired forces. Such tables include orthopedic tables, fracture tables and Jackson tables, all of which are quite expensive, cumbersome, and difficult to set up. Specialized personnel, such as operating assistants, are usually required in the process of setup and connecting the traction equipment to a patient. Such tables are not in the normal sense of the word portable, typically being heavy, large and permanently installed in a hospital or other treatment facility. They do not lend themselves to use in ambulances, on gurneys or at locations outside the hospital where application of traction forces to an individual may be called for.

DISCLOSURE OF INVENTION

The present invention relates to a portable traction apparatus which is inexpensive and uncomplicated. The apparatus may be utilized in many different environments and locations, for example in ambulances, on gurneys or in association with beds, tables or other supports for the individual being treated. Because of its compact, portable and relatively light-weight nature, the apparatus may be utilized in virtually any environment or at any location. The apparatus can be used to apply traction forces to animals as well as to humans.

The portable traction apparatus of the present invention includes a support member. An elongated, double-ended traction arm is pivotally connected to the support member and mounted for movement with respect thereto about orthogonally disposed pivots.

Lock means is provided for selectively locking the traction arm against movement relative to the support member at selected orientations relative to the support.

Attachment means is connected to the support member for releasably attaching the support member to a structure.

Other features, advantages, and objects of the present invention will become apparent with reference to the following description and accompanying drawings.

BRIEF DESCRIPTION OF DRAWINGS

FIG. 1 is a perspective view of portable traction apparatus constructed in accordance with the teachings of the present invention;

FIG. 2 is a front, elevational view of the portable traction apparatus showing the traction arm thereof in alternate positions, one position depicted by solid lines and two other positions depicted by dash lines;

FIG. 3 is a cross-sectional view taken along line 3—3 in FIG. 1;

FIG. 4 is a side elevational view illustrating the apparatus attached to a bed and utilized to apply traction forces to the leg of an individual on the bed, the traction arm being shown in three alternate positions;

FIG. 5 is a perspective view illustrating a selected portion of the apparatus prior to assembly of the traction arm to the support member of the apparatus;

FIG. 6 is a perspective view of the lower end of the traction arm;

FIG. 7 is a perspective view illustrating the apparatus clamped to a horizontally disposed table portion, only a portion of the traction arm being illustrated;

FIG. 8 is a view similar to FIG. 7 but illustrating the apparatus clamped to a vertical post or leg;

MODES FOR CARRYING OUT THE INVENTION

Figure 9:
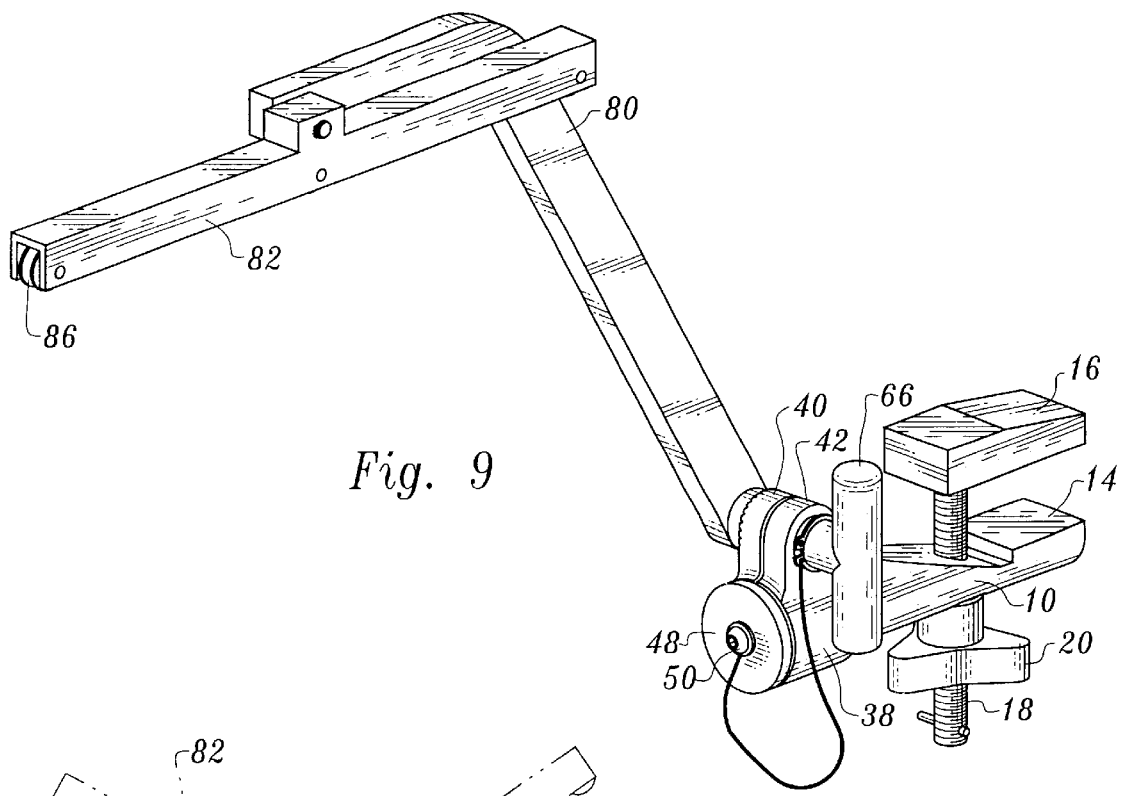
FIG. 9 is a view similar to FIG. 1 but illustrating an alternate embodiment of the apparatus.

One embodiment of the invention is illustrated in FIGS. 1–8. The apparatus includes a support 10 including a support shaft 12 (FIG. 3).

At the end thereof opposed to support shaft 12 the support 10 has a planar clamping surface 14. Positioned above the support is a clamp 16 having a bottom planar surface. Extending downwardly from clamp 16 is a threaded shaft 18 which passes through a throughbore formed in the support 10 and extends outwardly from the bottom thereof, as shown. The shaft 18 is threadedly engaged with a handle 20. Rotation of the handle 20 will cause the clamp 16 to move toward or away from the handle depending upon the direction of rotation of the handle, it being understood that the threaded shaft is not threadedly engaged with the support and is able to move freely up or down within the throughbore formed therein. A pin 22 is located at the lowermost shaft end to prevent the handle 20 from being disengaged therefrom.

The clamping arrangement just described can be utilized to attach the support to a wide variety of structures. In FIG. 7, for example, the apparatus is shown clamped to a table 26. In FIG. 8 the apparatus is shown clamped to a vertically disposed furniture leg 28. To prevent rotation of the shaft 18 relative to the support, a keyway 30 (see FIG. 7) extends along the length of the shaft, the keyway cooperating with a guide pin 32 extending inwardly into the throughbore occupying shaft 18 from the side of the support.

Positioned on and rotatable about support shaft 12 is a connector member 36. Connector member 36 includes sleeve member 38 and two spaced projections 40, 42 integrally connected to the sleeve member. The connector member 36 defines a gap 44, the projections 40, 42 being disposed on opposite sides of the gap. The gap 44 extends along the length of the sleeve member 38. In the absence of outside forces being applied to the connector member, the gap is opened to its maximum and the sleeve member is freely rotatable about support shaft 12.

An end cap 48 is secured to the end of support shaft 12 by a threaded fastener 50 to retain the connector member 36 on the support shaft.

A threaded lock shaft 52 extends through aligned openings formed in projections 40, 42. One such opening, opening 54, is shown in FIG. 5 and it is to be understood that a similar opening is formed in projection 42.

An elongated, double-ended traction arm 60 is mounted adjacent to and in engagement with projection 54. The traction arm 60 incorporates a boss 62 at the lower end thereof and a threaded hole 64 passes through the traction arm at that location. The distal end of threaded lock shaft 52 (the end spaced from handle 66 affixed to the threaded lock shaft) is positioned in threaded hole 64 to secure the traction arm 60 to the connector member. Until the traction arm 60 is lockingly engaged with connector member 36 in a manner which will be described below, the traction arm is free to pivot about the lower end thereof. This action is shown in FIG. 4 wherein the traction arm 60 is shown disposed in three different positions. Also, the traction arm is free to pivot about support shaft 12, as depicted in FIG. 2.

Locking of the traction arm against movement relative to the connector member 36 is effected by turning the threaded lock shaft 52 by handle 66 to bring the boss 62 into tight engagement with projection 40. More particularly, locking teeth 68 on projection 40 intermesh with similar teeth 70 on the outer surface of boss 62. Once the teeth of the traction arm and the projection 40 are brought into tight engagement, the traction arm is locked at a certain desired orientation with respect to the connector member.

Tightening of the traction arm 60 against projection 40 by rotation of threaded lock shaft 52 also causes the projections 40, 42 to move toward one another and narrow gap 44. During this operation, projection 42 engages handle 66. Closing of the gap 44 causes the sleeve member 38 to tighten about support shaft 12, thus locking the connector member (and traction arm 60) against rotatable movement about support shaft 12. In other words, the locking arrangement incorporated in the apparatus allows manipulation of a single threaded lock shaft 52 to lock the traction arm against movement about two orthogonally disposed pivots, one pivot being support shaft 12 and the other being orthogonally disposed threaded lock shaft 52.

In the arrangement illustrated, a retainer string 72 connects the handle 66 to the support 10 to prevent it from being lost or misplaced when the apparatus is disassembled.

Figure 10:
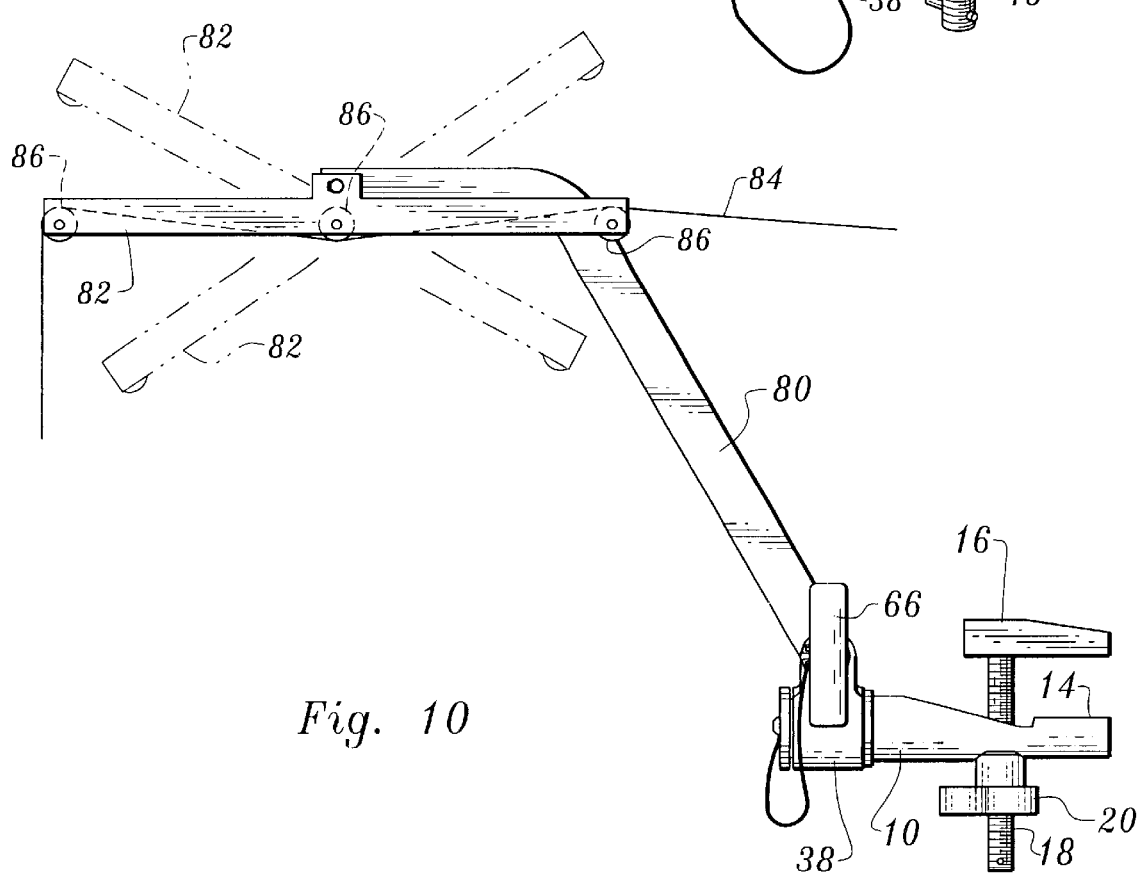
FIG. 10 is a side, elevational view of the apparatus of FIG. 9 in association with a line or cable employed to apply traction forces to a patient.

FIGS. 9 and 10 illustrate an alternative embodiment of the device that is in all respects the same as that shown in FIGS. 1–8 except for the shape of the traction arm and the fact that the traction arm pivotally supports a secondary arm. The traction arm of FIGS. 9 and 10 is identified by reference numeral 80 and the secondary arm pivotally connected thereto is identified by reference numeral 82. This arrangement is in the nature of a traveling traction setup, traction forces being applied to a patient by a line in the form of rope or cable 84 (FIG. 10) extending between the patient and a suspended weight, neither the patient nor weight being illustrated. Rollers 86 guide the line 84.

The invention claimed is:

1. Portable traction apparatus for applying traction forces to a human or animal body, said portable traction apparatus comprising, in combination:

a support member;

an elongated double-ended traction arm pivotally connected to said support member and mounted for movement with respect thereto about orthogonally disposed pivots;

lock means for selectively locking said traction arm against movement relative to said support member at selected orientations relative to said support member;

attachment means connected to said support member for releasably attaching said support member to a structure; and a connector member pivotally connecting said traction arm to said support member, said support member including a support shaft and said connector member positioned on and rotatable about said support shaft, said connector member comprising a sleeve member receiving said support shaft, said sleeve member defining a gap extending along the length of said sleeve member, said lock means being cooperable with said sleeve member to selectively alternatively narrow said gap to tighten said sleeve member against said support shaft and prevent rotation of said sleeve member on said support shaft or provide for expansion of said gap to loosen said sleeve member relative to said support shaft to allow rotation of said sleeve member on said support shaft, said sleeve member including two spaced projections disposed on opposite sides of said gap and defining generally aligned openings, said lock means comprising a threaded lock shaft extending through said openings, rotational movement of said threaded lock shaft resulting in either narrowing or expansion of said gap, said elongated traction arm defining a hole generally aligned with the openings in said projections, said threaded lock shaft located in said hole and connecting said elongated traction arm to said sleeve member, rotational movement of said threaded lock shaft in a direction causing narrowing of said gap to prevent rotation of said sleeve member on said support shaft substantially simultaneously causing locking engagement between said elongated traction arm and said sleeve member to prevent relative movement between said elongated traction arm and said sleeve member.

2. The portable traction apparatus according to claim 1 wherein said attachment means comprises a clamp.

3. The portable traction apparatus according to claim 1 wherein said elongated traction arm and one of the projections of said sleeve member include teeth which intermesh to lock said elongated traction arm against movement relative to said sleeve member.

4. The portable traction apparatus according to claim 3 wherein said hole in said elongated traction arm is threaded and located at an end of said elongated traction arm, said threaded lock shaft being threadedly engaged with said elongated traction arm in said hole.

5. The portable traction apparatus according to claim 1 wherein said threaded lock shaft is disposed orthogonally relative to said support shaft.

6. The portable traction apparatus according to claim 1 additionally comprising a secondary arm pivotally connected to said traction arm at a location spaced from said support member, said secondary arm having at least one rotatable roller element connected thereto for supporting a traction line.

* * * * *